United States Patent [19]
Bencini et al.

[11] Patent Number: 5,052,402
[45] Date of Patent: Oct. 1, 1991

[54] DISPOSABLE BIOPSY FORCEPS

[75] Inventors: Robert F. Bencini, Dracut; Barry D. Weitzner, Chelmsford, both of Mass.

[73] Assignee: C.R. Bard, Inc., Murray Hill, N.J.

[21] Appl. No.: 646,477

[22] Filed: Jan. 24, 1991

Related U.S. Application Data

[63] Continuation of Ser. No. 304,367, Jan. 31, 1989, abandoned.

[51] Int. Cl.⁵ .............................................. A61B 10/00
[52] U.S. Cl. .................................... 128/751; 606/206
[58] Field of Search ................ 128/751, 757; 604/22; 294/100; 606/206, 207, 208

[56] References Cited

U.S. PATENT DOCUMENTS

| | | | |
|---|---|---|---|
| 2,060,366 | 11/1936 | Dunlap | 128/321 |
| 2,113,246 | 4/1938 | Wappler | 128/321 |
| 2,518,994 | 8/1950 | Miller | 128/321 |
| 3,147,749 | 9/1964 | Marsh . | |
| 3,506,012 | 4/1970 | Brown . | |
| 3,628,522 | 12/1971 | Kato . | |
| 3,895,636 | 7/1975 | Schmidt . | |
| 3,924,608 | 12/1975 | Mitsui . | |
| 4,174,715 | 11/1979 | Hasson . | |
| 4,427,014 | 1/1984 | Bel et al. . | |
| 4,449,518 | 5/1984 | Konomura et al. . | |
| 4,506,669 | 3/1985 | Blake, III . | |
| 4,522,206 | 6/1985 | Whipple et al. . | |
| 4,646,751 | 3/1987 | Maslanka . | |
| 4,655,219 | 4/1987 | Petruzzi . | |
| 4,669,471 | 6/1987 | Hayashi . | |
| 4,686,865 | 8/1987 | Bonnet et al. . | |
| 4,721,116 | 1/1988 | Schintgen et al. . | |
| 4,763,668 | 8/1988 | Macer et al. | 606/206 X |
| 4,815,476 | 3/1989 | Clossick . | |
| 4,817,630 | 4/1989 | Schintgen et al. | 128/751 |
| 4,881,550 | 11/1989 | Kothe | 606/170 X |

FOREIGN PATENT DOCUMENTS 140951 4/1961 U.S.S.R. .

Primary Examiner—Michael H. Thaler
Attorney, Agent, or Firm—Wolf, Greenfield & Sacks

[57] ABSTRACT

A disposable biopsy forceps includes an elongate tubular member having proximal and distal ends. Manually operated actuating means is mounted to the proximal end of the flexible tubular member. A biopsy jaw assembly is mounted to the distal end of the tubular member and is operatively connected to the actuating means by a control wire extending through the tubular member. Several embodiments of jaw arrangements are disclosed. At least the cups and cutting rim portion of the cutting jaws is formed from an injection molded plastic capable of holding and retaining an edge sufficiently sharp to cut tissue.

22 Claims, 5 Drawing Sheets

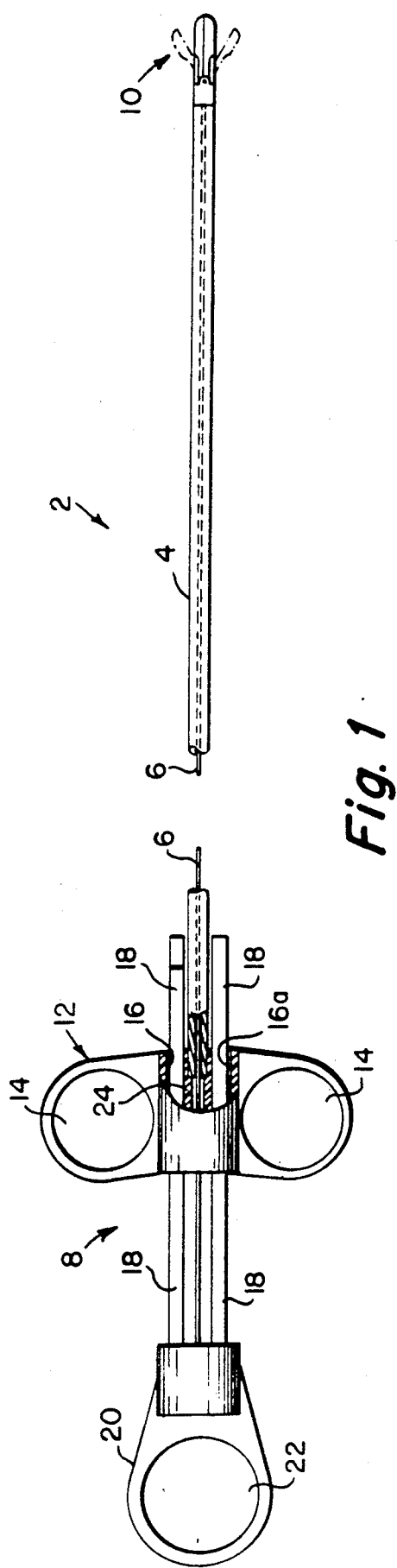
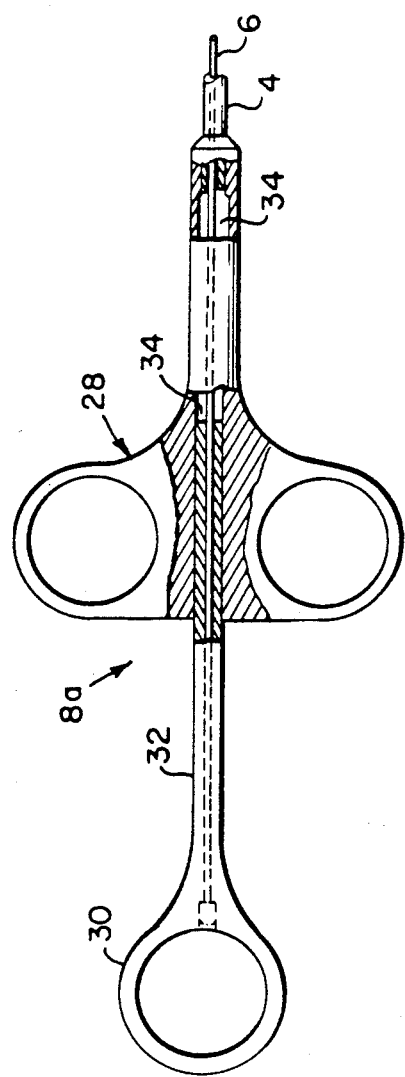
Fig. 1
Fig. 2

DISPOSABLE BIOPSY FORCEPS

This application is a continuation of application Ser. No. 304,367, filed Jan. 31, 1989, now abandoned.

FIELD OF THE INVENTION

The invention relates to biopsy forceps for taking small internal tissue samples from a patient.

BACKGROUND OF THE INVENTION

When making an endoscopic examination of a particular site in a patient s body, it is common for the physician to take at least one tissue sample from that site for analysis. A variety of such devices for taking of small tissue samples are in use. In general, such biopsy devices include a small diameter elongate catheter-like instrument adapted to be passed through a lumen in the endoscope, the device being longer than the endoscope so that its distal end can extend out of the distal end of the endoscope. The distal end of the device typically is provided with a pair of sharp jaws that can be open and closed to cut away a small sample of tissue to be investigated. The opening and closing of the jaws is controlled manually by the physician by manipulating controls at the proximal end of the device.

Such endoscopic biopsy procedures involve repeated insertion and removal of the device through the narrow endoscope channel when it is necessary to take multiple biopsies. The device must be sufficiently rugged to withstand such repeated use yet must be constructed so that it will not cause damage to any of the parts of the endoscope as it is advanced through the endoscopic channel.

Among the difficulties presented with such devices is that they typically are relatively expensive, partly because of the intricate work required to manufacture the miniature jaws and jaw actuating mechanisms. Additionally, the cutting edges of the jaw tend to become dull with use and require periodic sharpening, a procedure that involves considerable skill and a high degree of care because of the miniature size of the jaws Very slight errors in sharpening procedure can impair seriously the effectiveness of the jaws. Often, it is only possible to sharpen such a device a few times before its dimensions are so changed that it is no longer effective. When that occurs, it is common practice to replace the entire device Also among the difficulties presented by such endoscopic biopsy devices is that they are difficult to clean and sterilize. The jaw mechanisms define numerous crevices. Additionally, the elongate body of the device is made from a highly flexible tightly wound helical coil which provides numerous crevices for retaining debris or contaminants and the like.

It is believed that there is a need for a low cost, simple, disposable endoscopic biopsy device. It is among the general objects of the invention to satisfy that need.

SUMMARY OF THE INVENTION

In each of the several embodiments cf the invention, the device includes an elongate flexible solid wall tubular catheter formed from a plastic extrusion. A control wire extends through the catheter and is connected at its proximal end to an actuation means by which the physician may pull or push on the wire. The distal end of the device carries a pair of jaws each of which has at its end a sharp rimmed cup so that when the jaws are brought together, they may sever and retain a sample of tissue. Unlike the prior art biopsy devices, the embodiments of the present invention are free of complex linkages and multiple hinge points, the present invention incorporating either a single hinge point or a living hinge for mounting the jaws. In each embodiment, the jaws are caused to close by a longitudinally movable jaw actuator that is operated by the control wire In each embodiment, the jaw actuator engages the jaws to cause the jaws to close as the actuator moves in a distal direction. When the jaw actuator is retracted in a proximal direction, the jaws, which are biased in an open configuration, are permitted to open.

In two of the embodiments of the invention the jaws are connected by a single hinge pin and are biased apart by a spring. In another embodiment of the invention, the jaws are hinged together by a strip of spring metal. In another embodiment of the invention, the jaws are molded from plastic in a single integral unit which defines a living hinge between the jaws.

It is among the general objects of the invention to provide endoscopic biopsy devices having biopsy jaw arrangements that are of relatively simple inexpensive design.

Another object of the invention is to provide an endoscopic biopsy device of sufficiently low cost as to be disposable yet which may be reused if desired and, if reused, is easily cleaned and sterilized.

A further object of the invention is to provide an endoscopic biopsy device having a simplified, positive means for opening and closing its jaws.

Another object of the invention is to provide an endoscopic biopsy device in which the jaws, when closed, remain in the closed position until opened by the user.

DESCRIPTION OF THE DRAWINGS

The foregoing and other objects and advantages of the invention will be appreciated more fully from the following further description thereof, with reference to the accompanying drawings wherein:

FIG. 1 is a fragmented partly broken away illustration of one embodiment of an endoscopic biopsy device in accordance with the present invention;

FIG. 2 is a fragmented sectional illustration of the proximal end of an endoscopic biopsy device showing an alternative construction for the actuating means;

DESCRIPTION OF THE ILLUSTRATIVE EMBODIMENTS

Figure 3:
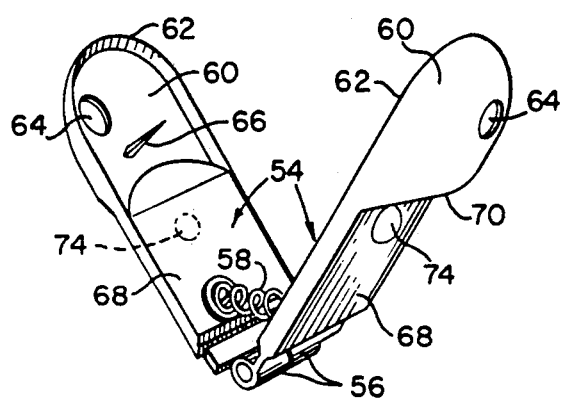
FIG. 3 is an exploded enlarged view of the distal end of the biopsy jaws and jaw actuator mechanism in accordance with one embodiment of the invention.
Figure 3:
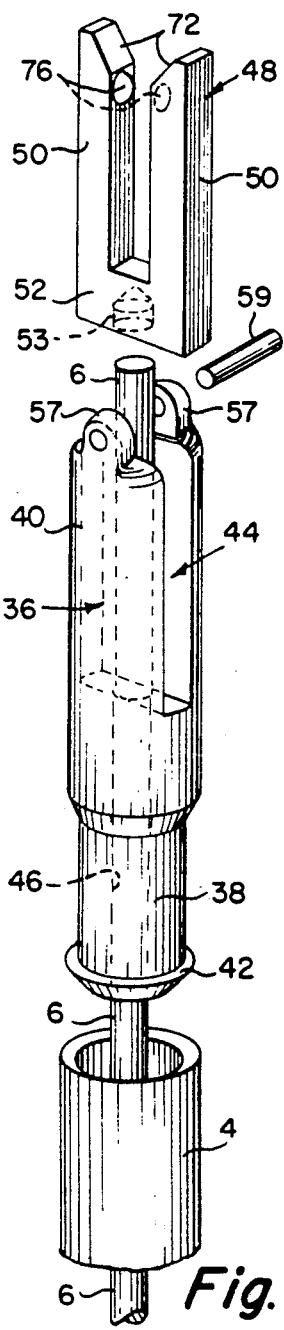

FIG. 1 shows one embodiment of the invention in which an elongate endoscopic biopsy device 2 includes an elongate flexible plastic tube 4. The tube 4 is formed preferably from polypropylene or other suitable plastic which will resist longitudinal stretching as a result of the axial loads applied to it by operation of the jaw. A control wire 6 which may be formed from stainless steel extends through the lumen in the plastic tube 4. The control wire 6 connects to an actuating means 8 at the proximal end of the device by which the physician controls the device. A pair of biopsy jaws 10 is mounted to the distal end of the plastic tube 4. The jaws 10 are operatively associated with the control wire 6 so that they may be closed or opened (as illustrated in phantom in FIG. 1) by operation of the control wire 6. When the jaws 10 are closed they define a diameter substantially the same as the tube 4 so that the entire device will fit slidably through the channel in the endoscope The dimensions of the channel in the endoscope will vary for different types of endoscopes. For example, endoscopes used in gastrointestinal environments typically have a biopsy channel 2.8 mm in diameter whereas endoscopes for pulmonary use typically have a biopsy channel 2.0 mm in diameter. Additionally, the lengths of such endoscopes varies according to their use. Pulmonary endoscopes are shorter than gastrointestinal endoscopes. By way of further example, the tube 4 of the present invention may be of the order of between 0.070" to 0.080" in diameter and may be between 100 cm to 240 cm in length, depending on the type and size of the endoscope with which it is to be used. Other lengths and diameters may be appropriate for other types of endoscopes which may have different lengths and channel sizes. It may be desirable, in use, to coat the outer surface of the tube 4 with a lubricious material. The diameter of the control wire 6 depends on the length of the device and, possibly, on the type of tissue which the device will be used to sample. The stiffness of the control wire is a function of its diameter. Preferably, the control wire usable for the particular type of endoscope should be the smallest diameter that will operate the jaws 10 so as not to adversely affect the flexibility of the device. By way of example, we have found that a control wire as small as 0.016" diameter may be effective to operate the jaws in a device 100 cm to 240 cm long. The control wire preferably is coated with Teflon (polytetrafluoroethylene) to enhance its ability to slide in the tube 4.

In the embodiment shown in FIG. 1, the actuating means 8 includes a stationary member 12 that is attached to the proximal end of the plastic tube 4. The stationary member 12 preferably is provided with a pair of finger holes 14. The stationary member 12 also is provided with a pair of longitudinally extending bores 16 and 16a which slidably receive a pair of rods 18. A thumb member 20 having a thumb hole 22 is attached to the proximal ends of the parallel rods 18. The proximal end of the pull wire 6 extends through an opening 24 in the stationary member 12 and is attached, at its proximal end, to the thumb member 20. From the foregoing, it will be appreciated that the proximal end of the biopsy device 2 can be operated with one hand, to pull the pull wire 6 proximally or push it distally. The distal end of the pull wire is connected to the biopsy jaws 10 in a manner described further below FIG. 2 illustrates an alternate actuating means 8a at the proximal end of the device. The actuating means 8a also includes a stationary member 28 and a thumb member 30. The thumb member 30 is disposed at the proximal end of a rod 32 which is slidably received within a bore 34 of the stationary member 28. The control wire 6 is connected at its proximal end to the thumb member 30 and extends distally through the bore 34 in the stationary member 28. The proximal end of the catheter tube 4 is secured in the distal end of the bore 34, the control wire 6 extending through the tube 4 as described above in connection with FIG. 1.

Figure 3A:
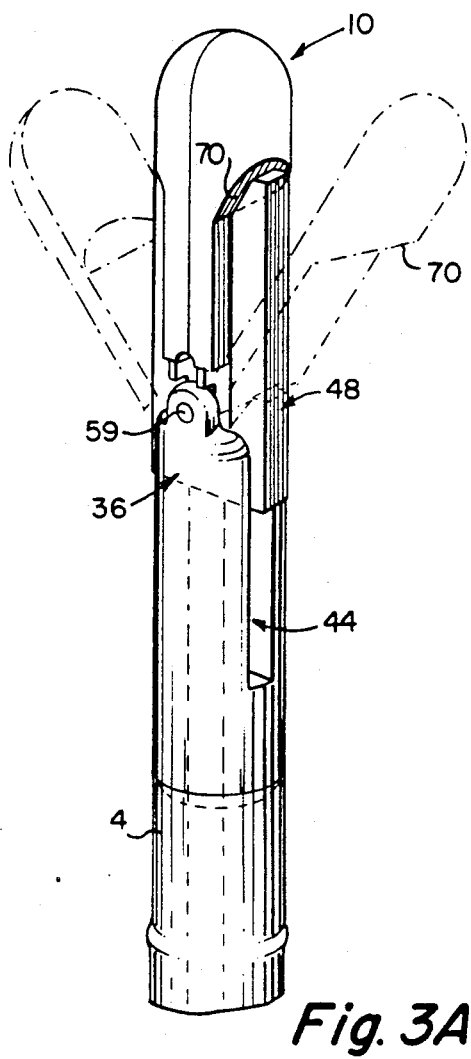
FIG. 3A is an enlarged illustration of the assembled device of FIG. 3 showing the jaws in closed position in solid lines and in the open position in phantom.

FIGS. 3 and 3A illustrate one embodiment of the biopsy jaw assembly. The assembly includes a generally cylindrical jaw support 36 having a proximal end 38 that fits securely within and may be adhesively attached to the distal end of the tube 4, and a distal cylindrical end 40. The proximal end of the jaw support 36 is of reduced diameter to fit within the lumen of the plastic tube 4 and may be provided with a barb-like circumferential flange 42 at its most proximal end which may securely engage and tend to dig into the inner surface of the lumen in the plastic tube 4 thereby to secure the jaw support in place. The distal end 40 of the jaw support 36 has a longitudinally extending slot 44. The inner end of the slot 44 communicates with the longitudinally extending bore 46 formed centrally through the proximal end 38 of the jaw support 36. The distal end of the control wire 6 extends through the bore 46 and into the slot 44 where it is connected to a jaw actuator 48. In this embodiment of the invention, the jaw actuator 48 is U-shaped having a pair of longitudinally extending spaced fingers 50 connected at a base 52. The base 52 has a proximally extending socket 53 in it bottom which receives the distal end of the control wire 6. The control wire 6 and base 52 may be secured together by brazing. The width of the jaw actuator 48 is such that it is slidably received within the longitudinal slot 44 of the jaw support 36. As will be described in further detail, the jaw actuator 48 may be reciprocated within the slot 44 to open and close the biopsy jaws. The jaw support 36 and jaw actuator 48 may be formed from an appropriate metal such as a surgical grade stainless steel.

Figure 4:
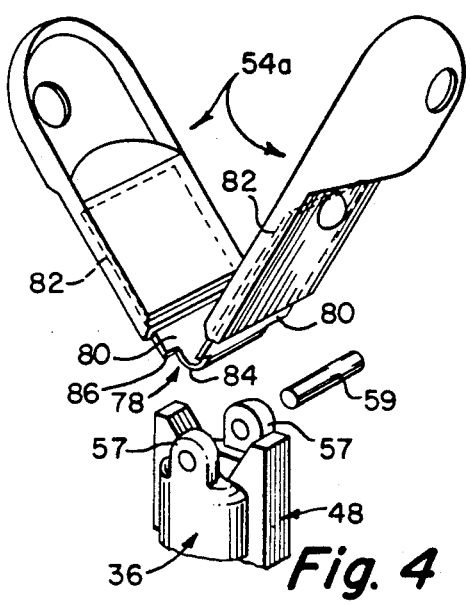
FIG. 4 is an exploded enlarged illustration of another embodiment of the biopsy jaws which the jaws are hinged together by a leaf spring.

As shown in FIGS. 3 and 4, the biopsy jaws include a pair of jaw members 54 and 54a which are preferably injection molded from a suitable plastic. The plastic should be capable of being molded to define and retain sharp cutting edges. We have found a suitable polymeric material commercially available from Du Pont under the 500 series Delrin polyoxymethylene, polyacetol. Alternately, the jaws 54 may be injection molded from a powdered metal in a scintering process. Parts made in such a process can be obtained for example, from Advanced Forming Technology, Inc., of Longmont, Co. The proximal ends of the jaw members 54 are provided with hinge elements 56. Jaw elements 54 are biased apart by a spring 58. The distal, outer, free ends of the jaw members are formed to define hollow cups 60 having inwardly facing sharp edges 62. The jaw members 54 are mounted by their hinge elements 56 to trunions 57 at the distal end of the jaw support 36 on opposite sides of the slot 44. A hinge pin 59 extends through the trunions 57 and the hinge elements 56.

When the jaw members 54 swing together, their sharp edges 62 meet with the cups 60 combining to enclose whatever tissue may have been severed and entrapped between the cups 60. The cups 60 may be provided with drain holes 64 to permit liquid to drain off. Barbs 66 may be formed on the inner surface of the cups 60 to further securely retain tissue entrapped between the cups 60.

The proximal portions 68 of the jaw members 54 are dimensioned so that they can be contained between the fingers 50 of the jaw actuator 48 when the jaw members 54 are brought together. Thus, as shown in solid in FIG. 3A, when the jaw actuator 48 is advanced distally, by operation of the control wire 6, the fingers 50 of the jaw actuator 48 engage the outwardly facing surfaces of the proximal portions 68 of the jaw members 54 so that continued distal advancement of the jaw actuator 48 will cause the jaws 54 to swing to a closed position as shown in solid in FIG. 3A. In the embodiment shown in FIGS. 3 and 3A, a portion 70 of the outwardly facing surface of the cups 60 is beveled and defines a stop against which a similarly beveled surface 72 on the ends of the fingers 50 can bear. Engagement of the beveled ends 72 of the fingers 50 with the beveled surfaces 70 on the cups 60 serves to stop the distal advancement of the jaw actuator 48, the jaw members 54 being in their fully closed position. It will be appreciated from FIG. 3A that when the jaw actuator and jaws are in this position, the jaw members 54 are securely contained between the fingers 50 which lock the jaws in a closed position.

In order to provide a further latching effect, as well as to provide a distinct feel for the physician to confirm full closure of the jaw members 54, a dimple 74 may be formed in the outwardly facing surface of each of the jaw members, each of the dimples 74 being adapted to receive a protrusion 76 formed near the outer ends of each of the fingers. The fingers 50 are sufficiently resilient so that they may spread apart to permit the protrusions 76 to slide along the outwardly facing surfaces of the proximal portions 68 of the jaw members 54. When the protrusions 76 engage the dimples 74, they do so in somewhat of a snap fit that can be detected at the actuating means 8, by the physician to provide confirmation that the jaws are closed and locked. FIG. 4 illustrates a modified embodiment of the jaw assembly. In this embodiment, the jaw members 54a are hinged together by a one-piece leaf spring hinge 78. The spring metal hinge 78 includes tongues 80 that are received in slots 82 formed in the jaw members 54a. The jaw members 54a may be injection molded from plastic or metal with the tongues 80 being molded into the jaw members 54a. The mid-portion of the leaf spring 78 is of reduced width so that it can fit between the trunions 57 of jaw support 36. The juncture of the tongues 80 with the central portion 84 of the leaf spring 78 defines a shoulder 86 which overlaps the trunions 57. The jaw arrangement of FIG. 4 is retained between the trunions by hinge pin 59 which overlies the central portion 84 of the leaf spring 78 and is supported by the trunions 57. The actuation of the embodiment shown in FIG. 4 is the same as that described above in connection with the embodiment of FIG. 3.

Figure 5:
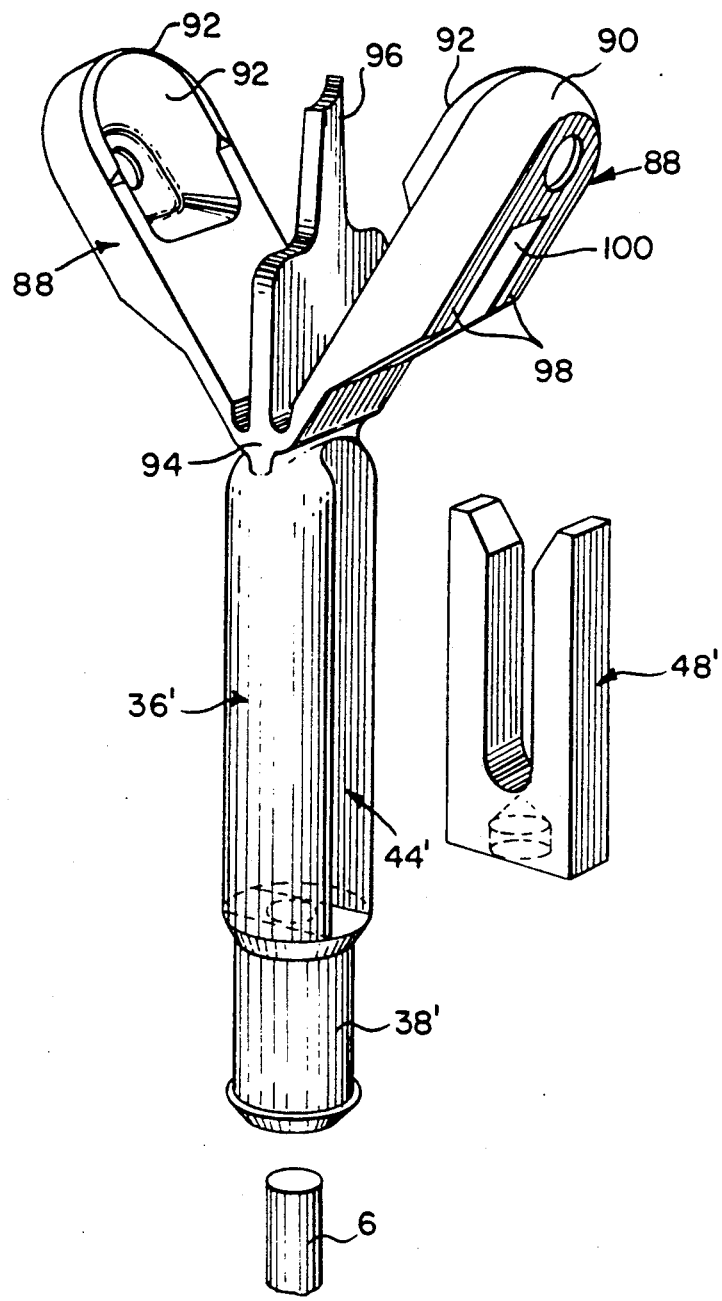
FIG. 5 is an exploded enlarged view of a biopsy jaw element in accordance with another embodiment of the invention in which the jaws are molded together from plastic and are hinged together by a living hinge.
Figure 5A:
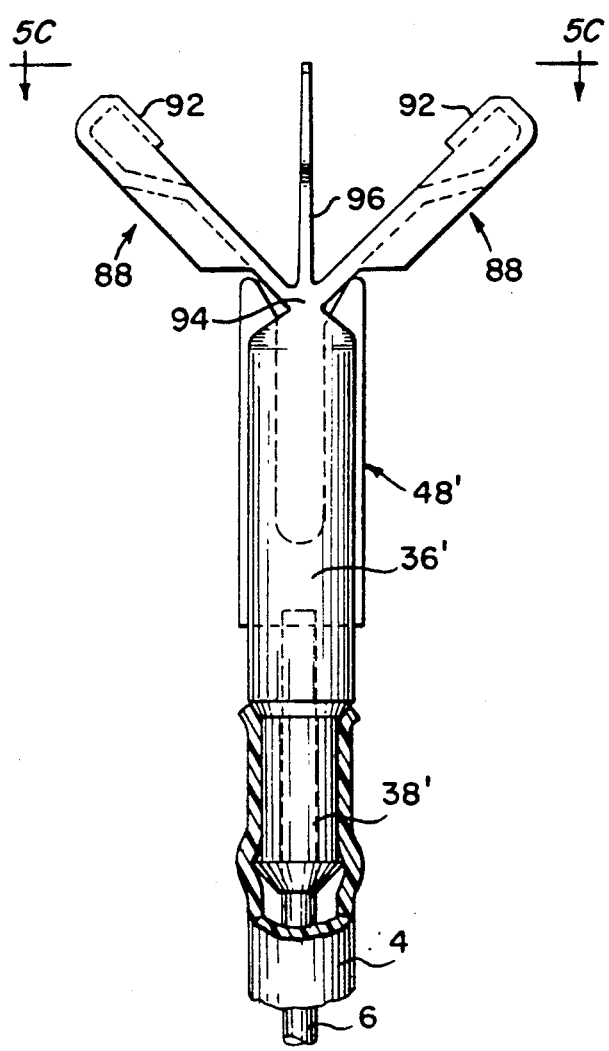
FIG. 5A is an enlarged side view of the assembled device of FIG. 5 illustrating the jaws in an open configuration.

FIG. 5 shows another embodiment of the invention in which the jaws 88 and jaw support 36' are molded from a suitable plastic such as Delrin, in a single piece. In this embodiment of the invention, the cylindrical jaw support 36' and longitudinal slot 44' are of the same configuration as described above in connection with the embodiment of FIG. 3 except that it is injection molded from plastic integrally with the jaw members 88. In this embodiment, no hinge pins or trunions are utilized, the jaw members 88 being molded integrally with the jaw support 36'. The jaw members 88 are molded to include cups 90 having sharp cutting edges 92 which function in the same manner as described above with the embodiments of FIG. 3. The jaw members 88 are molded integrally with jaw support 36' and are attached to the distal end of the jaw support 36' at a common juncture 94. The thickness of the plastic material adjacent the common juncture is controlled so as to define a resilient living hinge which will normally bias the jaw members 88 in an open configuration as shown in FIGS. 5 and 5A. In this embodiment of the invention, a distally extending spike 96 may be molded integrally with the jaw members 88 extending distally from the common juncture 94. The spike 96 serves to further secure a tissue sample captured between the cups 90, serving a function similar to that of the barbs 66 in the embodiment shown in FIG. 3.

The slot 44' receives the jaw actuator 48' in the same manner as corresponding elements in the embodiment described in FIG. 3. In this embodiment, the jaw members 88 may be provided with stiffening ribs 98 on opposite sides of the region engaged by the jaw actuator 48'. The stiffening ribs 98 define a slot 100 which receives the fingers of the jaw actuator 48'.

FIG. 5A illustrates the embodiment of FIG. 5 with the jaw actuator 48' in its proximal, retracted position and with the jaw members 88 in their open position. When the jaw members 88 are open, the spike 96 will be exposed. The spike 96 may be used to stabilize the distal end of the device in tissue to be sampled. The spike 96 also may serve as a skewer to pass through and retain cut tissue samples while the biopsy device continues to take additional tissue samples.

Figure 5B:
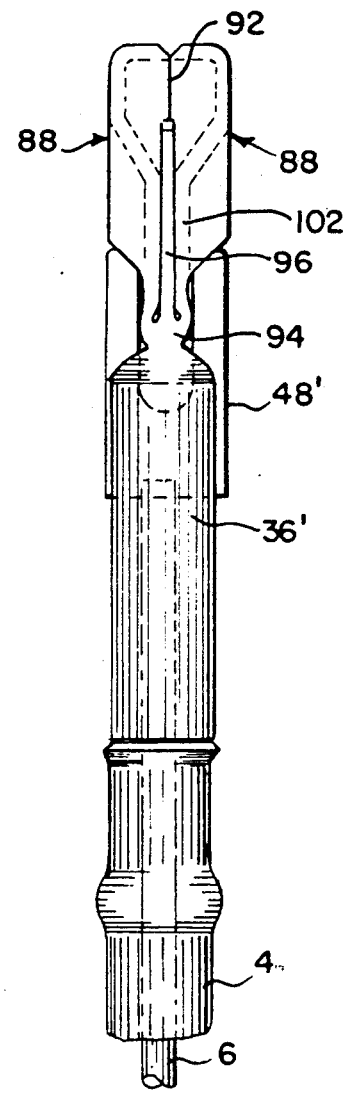
FIG. 5B is an enlarged illustration of the device of FIG. 5 showing the jaws in closed configuration.
Figure 5C:
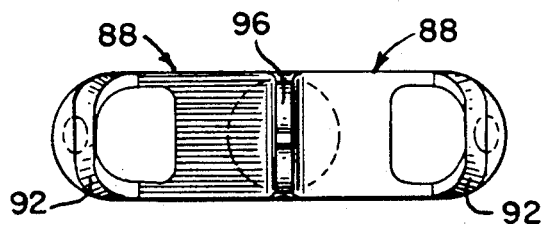
FIG. 5C is an enlarged top view of the jaws of FIG. 5A.

FIG. 5B illustrates the configuration of the device with the actuator 48' extended distally to draw the jaw members 88 together. It may be noted that in this embodiment, the parts are molded so that a clearance is left between the proximal portions 102 of the jaw members 88 so that they do not interfere with the central spike 96. The cutting edges 92 are raised somewhat so that they will engage each other and effect a complete severing of tissue. The one-piece molded embodiment of FIG. 5 is formed from a plastic that is relatively hard and capable of defining a good cutting edge 92 such as Delrin, described above. The Delrin material has a suitable combination of properties necessary to form a sharp cutting edge as well as to provide the resiliency required for the living hinge. We have found that a jaw assembly molded in a single piece from Delrin has good elastic memory retention during at least thirty opening and closing cycles of the jaws which is well in excess of the normally required number of openings and closing cycles that can be expected with a single patient.

Figure 6:
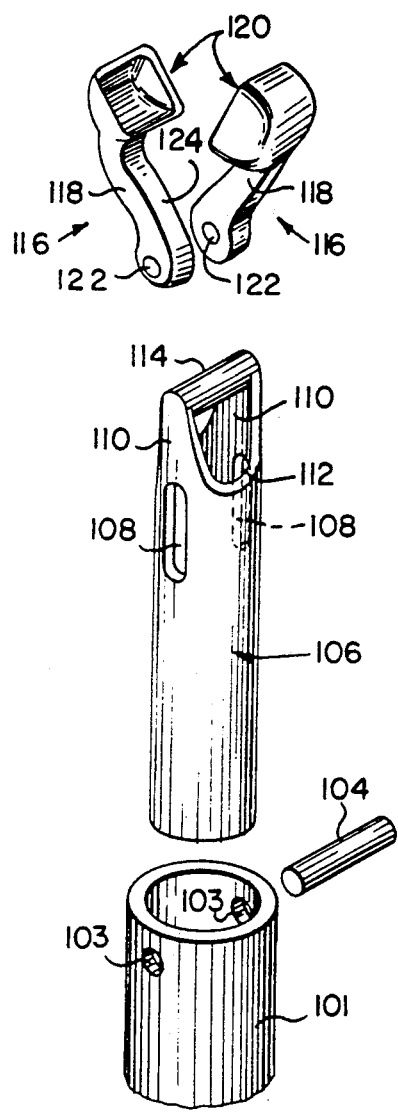
FIG. 6 is an exploded, enlarged view of a biopsy jaw configuration in accordance with another embodiment of the invention.
Figure 6A:
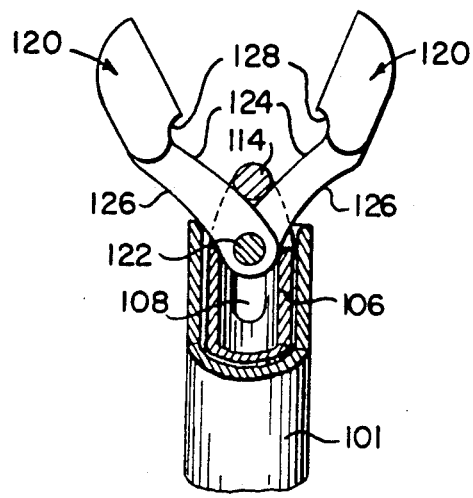
FIG. 6A is an enlarged side view of the assembled jaws of FIG. 6 showing the jaws in an open configuration.
Figure 6B:
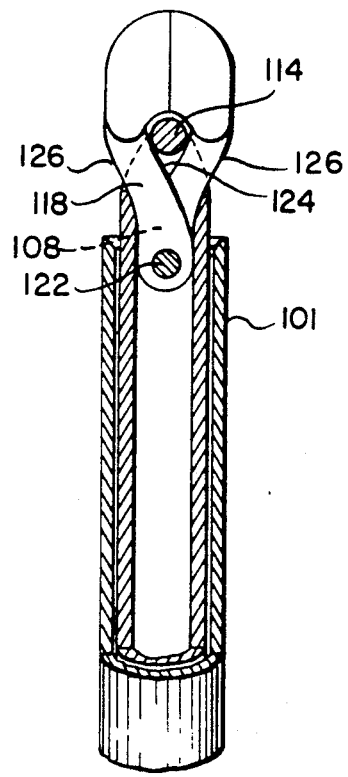
FIG. 6B is an enlarged side view of the jaws of FIG. 6 in closed configuration.

FIGS. 6, 6A and 6B illustrate another embodiment of the invention. In this embodiment a rigid tubular housing 101 is attached to the distal end of the tube 4 in the same manner as in the other embodiments. The housing 101 may be formed from plastic or metal, as desired. The housing 101 has a pair of diametrally opposed holes 103 formed at its distal end which are adapted to receive a pin 104. A tubular actuating member 106 is disposed slidably within the housing 101. The proximal end of the tubular actuating member 106 is secured to the distal end of the control wire 6 (not shown) as by brazing, soldering, suitable adhesive or the like. The actuating member 106 has a pair of diametrally opposed longitudinally extending slots 108 arranged to receive the pin 104. The slots 108 and pin 104 cooperate to limit the proximal and distal extremities of motion permitted to the actuator 106. The distal end of the actuator 106 includes a pair of distally extending projection 110 aligned with the slots 108. The cutouts 112 between the projection 110 are cut away to define openings through which the arms of a pair of jaws may extend. The outermost ends of the projections 110 are connected by a transverse bar 114.

A pair of biopsy jaws 116 having arms 118, cutting cups 120 at one end and pivot holes 122 at the other end are attached to the distal end of the device. The jaws 116 may be injection molded from a suitable plastic material such as Delrin or from powdered metal. As shown more clearly in FIGS. 6A and 6B, the proximal ends of the arms 118 are pivotably attached to the pin 104 by the holes 122. The arms 118 of the jaws 116 extend through the cutouts 112 and on opposite sides of the bar 114. As shown in FIG. 6A when the actuating member 106 is drawn proximally by pulling on the control wire 6, the bar 114 which extends between the arms 118 of the jaws 116 engages the inwardly facing surfaces 124 of the arms 118 to urge the arms 118 apart, thereby opening the jaws. When it is desired to close the jaws to cut a biopsy sample, the control wire is urged distally to move the actuator member 106 to the configuration illustrated in FIG. 6B. As the device advances from the configuration of FIG. 6A to that of FIG. 6B the bar 114 moves distally out of the way while the edges of the cutouts 112 move distally and engage the outwardly facing surfaces 126 of the arms 118. In doing so, the actuating member 106 urges the arms 118 together to close the jaws 116 in a cutting action. When the jaws 116 are closed, the bar 114 extends through a space defined by the recessed regions 128 of the arms 118, just proximal of the cutting cups 120. When in the closed configuration, the pin 104 is bottomed out against the proximal end of the slot 108. When the cups are in their most open position, the pin 104 is bottomed against the most distal end of the slot 108.

From the foregoing it will be appreciated that the invention provides biopsy catheters in which critical elements such as the jaws and cutting cups may be formed at a low cost by injection molding them from plastic. The actuating mechanisms for the cutting jaws are of relatively simple construction. Although the device is suitable for use as a disposable item, to be used only once, it may be sterilized and reused, depending on the condition of the cutting edges. Where the device has a smooth outer surface, free of the numerous crevices inherent in prior spring covered devices, there is less chance for entrapment of debris and contaminants. It should be understood, however, that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. A biopsy device comprising:
   a pair of biopsy jaws;
   an elongate flexible tube having a proximal end and a distal end;
   mounting means at the distal ends of the tube for supporting said pair of biopsy jaws for movement between open and closed positions;
   means for biasing the jaws toward their open position;
   a jaw actuating member carried at the distal end of the tube and controllably movable toward and away from the jaws, the actuating member being constructed and arranged to engage the jaws directly and to urge the jaws together when the actuating member is moved in one of said directions and for permitting the jaws to separate when moved in the other of said directions, said jaw actuating member being generally U-shaped and having a pair of distally extending fingers joined to each other at a base, the fingers being disposed to engage the outwardly facing surfaces of the jaws when the jaw actuating member is moved toward the jaws;
   actuating means at the proximal end of the tube and connected to the actuating member for moving the actuating member selectively in either of said directions; and
   detent means for engaging the jaw actuating member and jaws in the closed position.

2. A biopsy device as defined in claim 1 wherein the detent means comprises snap fit means emitting a detectable signal.

3. A biopsy device comprising:
   a pair of biopsy jaws;
   an elongate flexible tube having a proximal end and a distal end;
   a jaw actuating member carried at the distal end of the tube and controllably movable toward and away from the jaws, the actuating member being constructed and arranged to engage the jaws directly and to urge the jaws together when the actuating member is moved in one of said directions and for permitting the jaws to separate when moved in the other of said directions, said jaw actuating member being generally U-shaped and having a pair of distally extending fingers joined to each other at base, the fingers being disposed to engage the jaws when the jaw actuating member is moved toward the jaws;
   actuating means at the proximal end of the tube and connected to the actuating member for moving the actuating member selectively in either of said directions;
   mounting means at the distal end of the tube for supporting said pair of biopsy jaws for movement between open and closed position, said mounting mean comprising a jaw support mounted to the end of the flexible tube, a longitudinally extending slot formed in the jaw support to receive the U-shaped actuating member so that the U-shaped jaw actuating member is movably mounted on the jaw support for movement in a proximal and distal direction, the jaws being mounted to the distal end of the jaw support; and
   means for biasing the jaws toward their open position.

4. A biopsy device as defined in claim 3 further comprising:
   the fingers of the jaw actuating member engage the outwardly facing surfaces of the jaws.

5. A biopsy device as defined in claim 4 further comprising:

detent means for engaging the jaw actuating member and jaws in the closed position.

6. A biopsy device as defined in claim 3 further comprising:
the means connecting the actuating means to the jaw actuating member comprises a control wire attached to the base of the actuating member.

7. A biopsy device as defined in claim 6 wherein the control wire passes through the jaw support.

8. A biopsy device comprising:
a pair of biopsy jaws;
an elongate flexible tube having a proximal end and a distal end;
mounting means at the distal end of the tube for supporting said pair of biopsy jaws for movement between open and closed position;
a jaw actuating member carried at the distal end of the tube and controllably movable toward and away from the jaws, the actuating member being constructed and arranged to urge the jaws together when the actuating member is moved in one of said directions and for permitting the jaws to separate when moved in the other of said directions;
actuating means at the proximal end of the tube and connected to the actuating member for moving the actuating member selectively in either of said directions;
wherein the mounting means for the jaws comprises:
a tubular housing attached to the distal end of the tube, the housing having a pair of diametrally opposed holes formed adjacent the end thereof;
the actuating member being movable longitudinally within the tubular housing and having a pair of longitudinally extending diametrally opposed slots registrable with the holes in the tube;
a pin connected to the holes in the tube and secured thereto, the pin extending through the diametrally opposed slots in the actuating member;
the upper end of the actuating member having a diametrally extending bar and defining a pair of openings on opposite sides of said bar;
said jaws being pivotably attached at their proximal ends to the pivot pin and extending distally through the openings on opposite sides of said bar;
the distal ends of the jaws each carrying a cup defined by a cutting edge;
said housing, actuating member and jaws being constructed and arranged so that when the actuating member is moved in a proximal direction the bar will engage the facing sides of the arms and spread the arms apart to an open position and when the actuating member is moved to a distal position, it engages the outwardly facing surfaces of the arms to urge them together, the proximal ends of the arms being received in the hollow of the tubular actuating member;
the facing surfaces of the arms being formed to define a space receptive to the cross bar when the jaws are in their closed position.

9. A biopsy device as defined in claim 8 wherein each of the biopsy jaws includes a cup defined by a sharp rim, said cup and rim being injection molded from a polymeric material.

10. Biopsy forceps comprising:
an elongate flexible tube having a proximal end and a distal end;
a V-shaped jaw structure having a pair of opposing biopsy jaws connected together by a hinge at one end;
means connecting the hinge to the distal tube end;
an actuator fork slidably with respect to the distal tube end, said fork having a pair of fingers, each of said fingers bearing against one of said biopsy jaws at a point distal of the hinge;
an operating mechanism connected to the tube proximal end; and
shaft means positioned within the tube and connecting the operating mechanism to the actuator fork so that the operating mechanism pushes the shaft mans through the tube towards the distal tube end causing the actuator fork fingers to bear against, and close, the biopsy jaws.

11. Biopsy forceps as defined in claim 10 wherein the elongate flexible tube is sufficiently inelastic as to be non-distendable.

12. Biopsy forceps as defined in claim 10 wherein said jaws are connected to each other at a pin hinge connection, the pin being connected to the distal end of the tube.

13. Biopsy forceps as defined in claim 10 wherein said connecting means comprises:
a rigid jaw support connected to the distal tube end and to the hinge, the jaw support having a longitudinally extending slot formed therein to receive the actuator fork.

14. Biopsy forceps as defined in claim 13 further comprising:
a distally extending spike molded integrally and extending distally from the juncture of the hinge and the jaw support.

15. Biopsy forceps according to claim 10 further comprising means connected to the jaw structure to bias the pair of jaws apart from each other.

16. Biopsy forceps according to claim 15 wherein the V-shaped jaw structure, the bias means and the connecting means are molded from a single piece of polymeric material.

17. Biopsy forceps according to claim 10 wherein the tube is formed of a polymeric material.

18. Biopsy forceps according to claim 10 wherein the V-shaped jaw structure is molded from a single piece of polymeric material.

19. Biopsy forceps according to claim 10 wherein the actuator fork slides over the hinge of V-shaped jaw structure so that the fingers bear on the jaws and cause the jaws to close.

20. Biopsy forceps according to claim 10 wherein each of said pair of jaws has a cup with a sharp rim formed at the free end thereof.

21. Biopsy forceps according to claim 20 further comprising a tissue retention spike formed in at least one of the cups.

22. Biopsy forceps according to claim 10 wherein said hinge is a flat strip of spring material.

* * * * *

UNITED STATES PATENT AND TRADEMARK OFFICE
CERTIFICATE OF CORRECTION

PATENT NO.  : 5,052,402
DATED       : October 1, 1991
INVENTOR(S) : Robert F. Bencini and Barry D. Weitzner It is certified that error appears in the above-identified patent and that said Letters Patent is hereby corrected as shown below:

In column 10, line 10, delete "slidably" and insert --slidable--.

In column 10, line 19, delete "mans" and insert --means--.

Signed and Sealed this

Twenty-first Day of June, 1994

Attest:

BRUCE LEHMAN

*Attesting Officer*  *Commissioner of Patents and Trademarks*